United States Patent [19]

Anderson et al.

[11] Patent Number: 4,522,647

[45] Date of Patent: Jun. 11, 1985

[54] SUBSTITUTED PHENOXYALKANEDIONES AND THEIR HERBICIDAL METHOD OF USE

[75] Inventors: Richard J. Anderson, Palo Alto; Shy-Fuh Lee, Sunnyvale, both of Calif.

[73] Assignee: Zoecon Corporation, Palo Alto, Calif.

[21] Appl. No.: 508,971

[22] Filed: Jun. 29, 1983

Related U.S. Application Data

[63] Continuation-in-part of Ser. No. 403,836, Jul. 30, 1982, abandoned.

[51] Int. Cl.³ .................. C07D 213/26; C07D 213/64; A01N 43/40

[52] U.S. Cl. .................... 71/94; 546/157; 546/160; 546/288; 546/291; 546/296; 546/297; 546/300; 546/302; 546/304; 546/307; 546/312; 260/465 D; 564/433; 544/354; 548/115; 548/170; 548/221; 548/222; 548/329; 548/165; 560/21; 560/61; 560/62

[58] Field of Search .............. 546/288, 296, 297, 300, 546/302; 71/94

[56] References Cited

U.S. PATENT DOCUMENTS

| | | | |
|---|---|---|---|
| 3,379,752 | 4/1968 | Bolhofer | 560/53 |
| 4,133,675 | 1/1979 | Schurter et al. | 71/94 |
| 4,134,751 | 1/1979 | Nishiyama et al. | 71/94 |
| 4,348,221 | 9/1982 | Szczepanski | 71/94 |
| 4,408,076 | 10/1983 | Lee | 568/325 |
| 4,448,966 | 5/1984 | Lee | 546/302 |

*Primary Examiner*—Alan L. Rotman
*Attorney, Agent, or Firm*—Hana Dolezalova; Jacqueline S. Larson

[57] ABSTRACT

Substituted phenoxyalkanediones and intermediates therefor, and the use of said compounds for the control of weeds.

9 Claims, No Drawings

SUBSTITUTED PHENOXYALKANEDIONES AND THEIR HERBICIDAL METHOD OF USE

This is a continuation-in-part of Ser. No. 403,836, filed on July 30, 1982, now abandoned.

This invention relates to substituted phenoxyalkanediones and intermediates therefor, and the use of said compounds for the control of weeds.

More particularly, the substituted phenoxyalkanediones of the present invention are represented by the following formula (A):

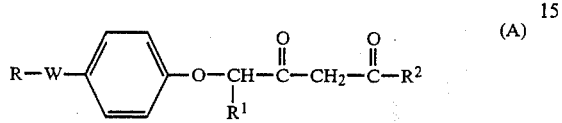

wherein,
R is

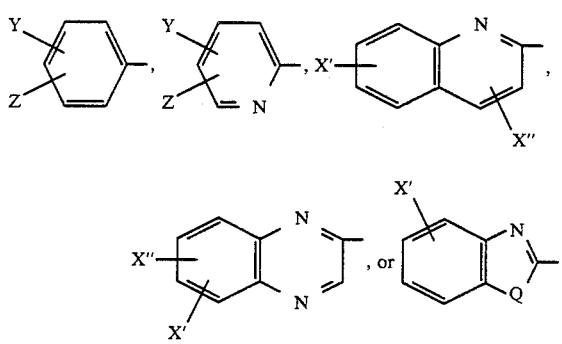

$R^1$ is hydrogen or lower alkyl;
$R^2$ is lower alkyl;
W is oxygen, sulfur or amino;
Q is oxygen or sulfur;
each of Y and Z is independently selected from hydrogen, lower alkyl, lower haloalkyl, lower alkoxy, lower haloalkoxy, halogen, nitro and cyano; and
each of X' and X" is independently selected from hydrogen, lower haloalkyl, lower alkoxy, halogen and nitro, provided that both X' and X" cannot be trifluoromethyl, methoxy or nitro.

In the description and claims hereinafter, each of $R$—$R^2$, Q, W, X', X" and Y and Z is as defined above, unless otherwise specified.

Compounds of the present invention of formula (A) can be synthesized as outlined below ($R^3$ is lower alkyl):

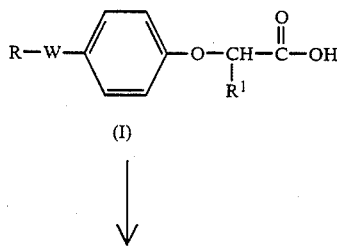

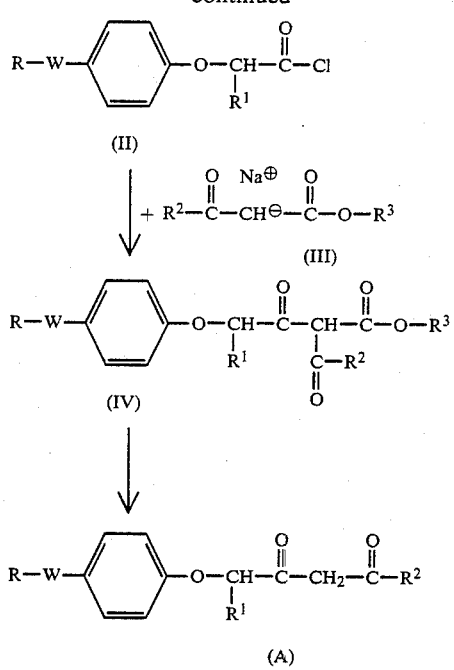

In the above synthesis, a carboxylic acid (I) is converted to its corresponding acid chloride (II) by reaction with oxalyl chloride or thionyl chloride and dimethylformamide (catalytic amount) in an organic solvent such as ether, benzene or tetrahydrofuran. The acid chloride (II) is reacted with the sodium salt of a β-ketoester (III) at reflux temperature and in a solvent such as benzene. The resulting carboxylate (IV) is heated at an elevated temperature, in the presence of sodium chloride and a solvent such as dimethylsulfoxide to yield an alkanedione of formula (A).

A carboxylic acid of formula (I) may be prepared by the reaction of a phenol (V) with a 2-halocarboxylate (VI; XX is Br, Cl or mesyloxy; $R^4$ is lower alkyl) at room temperature or above in the presence of a base such as alkali metal carbonate or alkali metal hydroxide to give a methyl carboxylate (VII). The carboxylate (VII) is hydrolyzed by reaction with sodium hydroxide followed by hydrochloric acid to give a carboxylic acid (I).

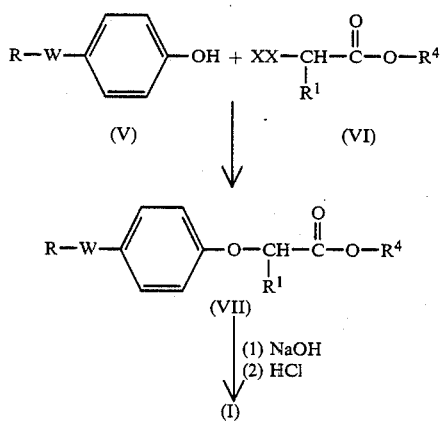

Alternatively, the compounds of formula (A) can be prepared from an aldehyde (XX) and an anion of the dimethylhydrazone of an appropriate ketone (XXI) following the method described by Corey and Enders, *Tetrahedron Letters*, 3–6 (1976) and *Tetrahedron Letters*, 11–14 (1976), to give the hydroxyketone (C) which is oxidized to the alkanedione (A) following the procedure of Corey and Kim, *JACS*, 94:7586 (1972).

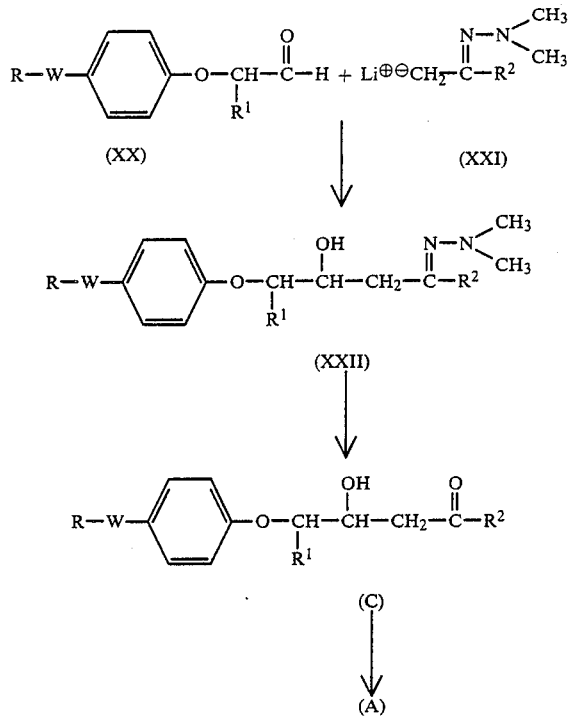

The dimethylhydrazone anion (XXI) can be prepared by reacting the appropriate ketone precursor with N,N-dimethylhydrazine [cf., A. C. Day and M. Whiting, *Org. Synthesis* 50:3 (1970)], and treating the resulting dimethylhydrazone of the ketone with n-butyllithium and tetrahydrofuran (THF) or with lithiumdiisopropylamide (LDA) and THF at a low temperature.

The following terms, wherever used in the description herein and in the appended claims, have the meaning defined below, unless otherwise specified hereinafter.

The term "lower alkyl" refers to an alkyl group, straight or branched, having a chain length of one to eight carbon atoms. The term "lower haloalkyl" refers to a lower alkyl group substituted with one to three halogen atoms.

The term "lower alkoxy" refers to an alkoxy group, straight or branched, having a chain length of one to eight carbon atoms. The term "lower haloalkoxy" refers to a lower alkoxy group substituted with one to three halogen atoms.

Many of the compounds of formulas (IV) and (C) are novel compounds and are included within the scope of the present invention.

The compounds of the present invention of formulas (A), (C) and (IV) have one or more asymmetric carbon atoms. The present invention includes each of the optical isomers and racemic mixtures thereof. In the examples hereinafter, unless otherwise specified, the compound prepared is a racemic mixture.

The novel compounds of formulas (A), (C) and (IV) are useful for the control of weeds, using pre- and/or post-emergent treatments. The compounds can be applied in the form of dusts, granules, solutions, emulsions, wettable powders, flowables and suspensions. Application of a compound of the present invention is made according to conventional procedure to the weeds or their locus using an herbicidally effective amount of the compounds, usually from about one-half or less to ten pounds per acre.

While some of the compounds of the present invention have activity on broad leaf plants, the compounds, in general, demonstrate a higher level of herbicidal activity on the grass weeds.

Methods of preparing herbicidal formulations which can be used with a compound of the present invention are described in the literature along with suitable liquid and solid carriers, such as in U.S. Pat. Nos. 4,192,669 and 4,163,661, which are incorporated herein by reference. The optimum usage of a compound of the present invention is readily determinable by one of ordinary skill in the art using routine testing such as greenhouse testing and small plot testing.

The compounds of the present invention, in view of their broadspectrum grass weed herbicidal activity, can be advantageously combined with broadleaf weed herbicides for broad-spectrum postemergence weed control in most broadleaf crops. Examples of herbicides which can be combined with a compound of the present invention include glyphosate, bentazone, diuron, paraquat, 2,4-D, 2,4-DB, diquat, endothal, dinoseb, dicamba, norflurazon, nitrofen, cyanozine, methazole, mefluidide, metribuzin, cycloate, fluometuron, linuron, dalapon, bifenox and alachlor for controlling a broad spectrum of weeds.

The term "herbicide," as used herein, refers to an active ingredient which modifies the growth of plants because of phytotoxic or plant growth regulating properties so as to retard the growth of the plant or damage the plant sufficiently to kill it.

The substituted phenoxyalkanediones of the present invention are tautomeric; that is, they exist in a state of equilibrium between the forms of formula (A) and formula (B).

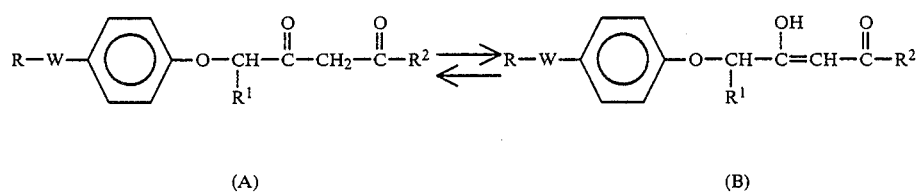

This is known in the chemical art as keto-enol tautomerism. The compounds of the present invention exist predominantly in the enolic, or formula (B), form. However, for the sake of consistency and simplicity, the compounds are described and named by formula (A). Both forms (A) and (B) are embraced by this invention.

The following examples are provided to illustrate the practice of the present invention. Temperature is given in degrees Centigrade. "RT" means room temperature.

EXAMPLE 1

Oxalyl chloride (1.56 g, 1.1 ml, 12.32 mmol) is added to a stirring solution of 2-[4-(4-trifluoromethylphenoxy)phenoxy]propionic acid (2.00 g, 6.16 mmol), dimethylformamide (DMF; 4 drops) and ether (50 ml). The mixture is stirred at RT for 3 hours. Insoluble material is filtered off and solvent is removed in vacuo to give 2-[4-(4-trifluoromethylphenoxy)phenoxy]propionic acid chloride.

A sodium salt solution of methylacetoacetate is prepared by dissolving methylacetoacetate (1.12 ml, 10.40 mmol) in benzene (25 ml). Sodium (0.76 g, 7.00 mmol) is added and the mixture is heated under reflux for about 1.5 hours.

The above acid chloride, taken up in benzene, is added dropwise to the chilled sodium salt of methylacetoacetate in benzene, and the mixture is heated under reflux for 2.5 hours. The reaction mixture is washed with water and dried over sodium sulfate, and the benzene is removed by evaporation. The crude product is purified by preparative thin layer chromatography (prep. TLC; silica gel developing with 50% ethyl acetate/hexane) to give methyl 2-acetyl-4-[4-(4-trifluoromethylphenoxy)phenoxy]-3-oxopentanoate (cpd. 1, Table A).

A mixture of the above pentanoate (0.30 g, 0.70 mmol), dimethylsulfoxide (DMSO; 3 ml), sodium chloride (0.40 g) and water (1 drop) is heated at 130° under $N_2$ for 5 hours. The reaction mixture is diluted with water and extracted with ether. The ether extracts are washed with water, dried and evaporated to dryness. Purification by prep. TLC gives 5-[4-(4-trifluoromethylphenoxy)phenoxy]-2,4-hexanedione (cpd. 1, Table B).

nmr (CDCl$_3$) δ 1.53 (d, 7 Hz, 3H, —OCH(CH$_3$)—), 2.05 (s, 3H, —C(O)—CH$_3$) and 4.57 (q, 1H, —OCH(CH$_3$)—).

EXAMPLE 2

Following the procedure of Example 1, each of the carboxylic acids under column I is reacted with oxalyl chloride to give the corresponding acid chloride, which is then reacted with the sodium salt of methylacetoacetate to give the acid ester in Table A. Each ester is heated with DMSO and NaCl to give the final dione in Table B.

I 2. 2-[4-(2-chloro-4-trifluoromethylphenoxy)phenoxy]propionic acid
3. 2-[4-(2,4-dichlorophenoxy)phenoxy]propionic acid
4. 2-[4-(2-nitro-4-trifluoromethylphenoxy)phenoxy]propionic acid
5. 2-[4-(2-methoxy-4-methylphenoxy)phenoxy]propionic acid
6. 2-[4-(2-fluoro-4-trifluoromethylphenoxy)phenoxy]propionic acid
7. 2-[4-(2-chloro-4-trifluoromethylphenylthio)phenoxy]propionic acid
8. 2-[4-(4-trifluoromethylphenylthio)phenoxy]propionic acid
9. 4-(4-trifluoromethylphenoxy)phenoxyacetic acid
10. 4-(2-chloro-4-trifluoromethylphenoxy)phenoxyacetic acid
11. 2-[4-(4-trifluoromethylanilino)phenoxy]propionic acid
12. 2-[4-(2-nitro-4-trifluoromethylanilino)phenoxy]propionic acid
13. 2-[4-(2,4-dichloroanilino)phenoxy]propionic acid
14. 2-[4-(2-bromo-4-chloroanilino)phenoxy]propionic acid
15. 2-[4-(4-chlorophenoxy)phenoxy]propionic acid

EXAMPLE 3

Following the procedure of Example 1, 2-[4-(4-trifluoromethylphenoxy)phenoxy]propionic acid chloride is added to the sodium salt of methyl propionylacetate in benzene to give methyl 2-propionyl-4-[4-(4-trifluoromethylphenoxy)phenoxy]-3-oxopentanoate (cpd. 16 in Table A). This pentanoate is then heated with DMSO and NaCl to give 2-[4-(4-trifluoromethylphenoxy)phenoxy]-3,5-heptanedione (cpd. 16, Table B).

TABLE A $$Z-\underset{\underset{Z}{\bigcirc}}{\overset{Y}{\bigcirc}}-W-\bigcirc-O-\underset{R^1}{\overset{}{C}H}-\overset{O}{\overset{\|}{C}}-\underset{\overset{\|}{C}-R^2}{\overset{}{C}H}-\overset{O}{\overset{\|}{C}}-O-R^3 \quad (VIII)$$

| Cpd | Z | Y | W | R$^1$ | R$^2$ | R$^3$ |
|---|---|---|---|---|---|---|
| 1 | CF$_3$ | H | O | CH$_3$ | CH$_3$ | CH$_3$ |
| 2 | CF$_3$ | Cl | O | CH$_3$ | CH$_3$ | CH$_3$ |
| 3 | Cl | Cl | O | CH$_3$ | CH$_3$ | CH$_3$ |
| 4 | CF$_3$ | NO$_2$ | O | CH$_3$ | CH$_3$ | CH$_3$ |
| 5 | CH$_3$ | OCH$_3$ | O | CH$_3$ | CH$_3$ | CH$_3$ |
| 6 | CF$_3$ | F | O | CH$_3$ | CH$_3$ | CH$_3$ |
| 7 | CF$_3$ | Cl | S | CH$_3$ | CH$_3$ | CH$_3$ |
| 8 | CF$_3$ | H | S | CH$_3$ | CH$_3$ | CH$_3$ |
| 9 | CF$_3$ | H | O | H | CH$_3$ | CH$_3$ |
| 10 | CF$_3$ | Cl | O | H | CH$_3$ | CH$_3$ |
| 11 | CF$_3$ | H | NH | CH$_3$ | CH$_3$ | CH$_3$ |
| 12 | CF$_3$ | NO$_2$ | NH | CH$_3$ | CH$_3$ | CH$_3$ |
| 13 | Cl | Cl | NH | CH$_3$ | CH$_3$ | CH$_3$ |
| 14 | Cl | Br | NH | CH$_3$ | CH$_3$ | CH$_3$ |
| 15 | Cl | H | O | CH$_3$ | CH$_3$ | CH$_3$ |
| 16 | CF$_3$ | H | O | CH$_3$ | CH$_2$CH$_3$ | CH$_3$ |

TABLE B $$Z-\underset{\underset{Z}{\bigcirc}}{\overset{Y}{\bigcirc}}-W-\bigcirc-O-\underset{R^1}{\overset{}{C}H}-\overset{O}{\overset{\|}{C}}-CH_2-\overset{O}{\overset{\|}{C}}-R^2 \quad (IX)$$

| Cpd | Z | Y | W | R$^1$ | R$^2$ |
|---|---|---|---|---|---|
| 1 | CF$_3$ | H | O | CH$_3$ | CH$_3$ |
| 2 | CF$_3$ | Cl | O | CH$_3$ | CH$_3$ |
| 3 | Cl | Cl | O | CH$_3$ | CH$_3$ |
| 4 | CF$_3$ | NO$_2$ | O | CH$_3$ | CH$_3$ |
| 5 | CH$_3$ | OCH$_3$ | O | CH$_3$ | CH$_3$ |
| 6 | CF$_3$ | F | O | CH$_3$ | CH$_3$ |
| 7 | CF$_3$ | Cl | S | CH$_3$ | CH$_3$ |
| 8 | CF$_3$ | H | S | CH$_3$ | CH$_3$ |
| 9 | CF$_3$ | H | O | H | CH$_3$ |
| 10 | CF$_3$ | Cl | O | H | CH$_3$ |
| 11 | CF$_3$ | H | NH | CH$_3$ | CH$_3$ |
| 12 | CF$_3$ | NO$_2$ | NH | CH$_3$ | CH$_3$ |
| 13 | Cl | Cl | NH | CH$_3$ | CH$_3$ |
| 14 | Cl | Br | NH | CH$_3$ | CH$_3$ |
| 15 | Cl | H | O | CH$_3$ | CH$_3$ |
| 16 | CF$_3$ | H | O | CH$_3$ | CH$_2$CH$_3$ |

EXAMPLE 4

Oxalyl chloride (279 mg, 0.19 ml, 2.2 mmol) is added to a stirring solution of 2-[4-(3-chloro-5-trifluoromethyl-2-pyridyloxy)phenoxy]propionic acid (400 mg, 1.1 mmol), DMF (1 drop) and ether (15 ml). The mixture is stirred at RT for approximately 3 hours. The solvent is removed to give the corresponding acid chloride.

Methylacetoacetate (209 mg, 0.19 ml, 1.8 mmol) is dissolved in benzene (20 ml), and to this solution is added sodium (4 mg, 1.8 mmol). The mixture is heated under reflux for 1.5–2 hours to give the sodium salt of methylacetoacetate.

The above acid chloride, in benzene, is added to the chilled sodium salt in benzene. The mixture is then heated under reflux for 3 hours. The reaction mixture is washed with water and dried over sodium sulfate, and the benzene is removed in vacuo. The crude product is purified by prep. TLC to give methyl 2-acetyl-4-[4-(3-chloro-5-trifluoromethyl-2-pyridyloxy)phenoxy]-3-oxopentanoate (cpd. 17, Table C).

nmr (CDCl$_3$)

$\tau$8.44 (d, 7Hz, 3H, —OCHC$\underline{H}_3$), 7.67 (s, 3H, —C(O)CH$_3$), 6.30 (s, 3H, —OCH$_3$), 4.64 (q, 1H, —OC$\underline{H}$CH$_3$), 3.14 (m, 4H, aromatic H), 2.19 (d, 1H, 2 Hz, pyridine H), 1.90 (bs, 1H, pyridine H).

A mixture of the above pentanoate (0.70 mmol), DMSO (3 ml), sodium chloride (0.40 g) and water (1 drop) is heated at 130° for 4–5 hours. The reaction mixture is diluted with water and extracted with ether. The ether extracts are washed with water, dried and evaporated to dryness. The crude product is purified by prep. TLC to give 5-[4-(3-chloro-5-trifluoromethyl-2-pyridyloxy)phenoxy]-2,4-hexanedione (cpd. 17, Table D), MS m/e 401.5 (M+).

EXAMPLE 5

Following the procedure of Example 4, each of the carboxylic acids under column II is reacted with oxalyl chloride to give the corresponding acid chloride, which is then reacted with the sodium salt of methylacetoacetate to give the carboxylic acid ester in Table C. Each ester is heated with sodium chloride and DMSO to give the final dione in Table D.

18. 2-[4-(5-trifluoromethyl-2-pyridyloxy)phenoxy]propionic acid
19. 2-[4-(3,5-dichloro-2-pyridyloxy)phenoxy]propionic acid
20. 2-[4-(3-fluoro-5-trifluoromethyl-2-pyridyloxy)phenoxy]propionic acid
21. 2-[4-(3-methoxy-5-methyl-2-pyridyloxy)phenoxy]propionic acid
22. 2-[4-(3-nitro-5-trifluoromethyl-2-pyridyloxy)phenoxy]propionic acid
23. 2-[4-(5-trifluoromethyl-2-pyridylthio)phenoxy]propionic acid
24. 2-[4-(3-chloro-5-trifluoromethyl-2-pyridylthio)phenoxy]propionic acid
25. 4-(3-chloro-5-trifluoromethyl-2-pyridyloxy)phenoxyacetic acid
26. 4-(5-trifluoromethyl-2-pyridyloxy)phenoxyacetic acid

EXAMPLE 6

Following the procedure of Example 4, 2-[4-(3-chloro-5-trifluoromethyl-2-pyridyloxy)phenoxy]propionic acid chloride is added to the sodium salt of methyl propionylacetate in benzene to give methyl 2-propionyl-4-[4-(3-chloro-5-trifluoromethyl-2-pyridyloxy)phenoxy]-3-oxopentanoate (cpd. 27, Table C). This pentanoate is then heated with sodium chloride and DMSO to give 2-[4-(3-chloro-5-trifluoromethyl-2-pyridyloxy)phenoxy]-3,5-heptanedione (cpd. 27, Table D).

TABLE C (X)

| Cpd | Z | Y | W | R$^1$ | R$^2$ | R$^3$ |
|---|---|---|---|---|---|---|
| 17 | CF$_3$ | Cl | O | CH$_3$ | CH$_3$ | CH$_3$ |
| 18 | CF$_3$ | H | O | CH$_3$ | CH$_3$ | CH$_3$ |
| 19 | Cl | Cl | O | CH$_3$ | CH$_3$ | CH$_3$ |
| 20 | CF$_3$ | F | O | CH$_3$ | CH$_3$ | CH$_3$ |
| 21 | CH$_3$ | OCH$_3$ | O | CH$_3$ | CH$_3$ | CH$_3$ |
| 22 | CF$_3$ | NO$_2$ | O | CH$_3$ | CH$_3$ | CH$_3$ |
| 23 | CF$_3$ | H | S | CH$_3$ | CH$_3$ | CH$_3$ |
| 24 | CF$_3$ | Cl | S | CH$_3$ | CH$_3$ | CH$_3$ |
| 25 | CF$_3$ | Cl | O | H | CH$_3$ | CH$_3$ |
| 26 | CF$_3$ | H | O | H | CH$_3$ | CH$_3$ |
| 27 | CF$_3$ | Cl | O | CH$_3$ | CH$_2$CH$_3$ | CH$_3$ |

TABLE D (XI)

| Cpd | Z | Y | W | R$^1$ | R$^2$ |
|---|---|---|---|---|---|
| 17 | CF$_3$ | Cl | O | CH$_3$ | CH$_3$ |
| 18 | CF$_3$ | H | O | CH$_3$ | CH$_3$ |
| 19 | Cl | Cl | O | CH$_3$ | CH$_3$ |
| 20 | CF$_3$ | F | O | CH$_3$ | CH$_3$ |
| 21 | CH$_3$ | OCH$_3$ | O | CH$_3$ | CH$_3$ |
| 22 | CF$_3$ | NO$_2$ | O | CH$_3$ | CH$_3$ |
| 23 | CF$_3$ | H | S | CH$_3$ | CH$_3$ |
| 24 | CF$_3$ | Cl | S | CH$_3$ | CH$_3$ |
| 25 | CF$_3$ | Cl | O | H | CH$_3$ |
| 26 | CF$_3$ | H | O | H | CH$_3$ |
| 27 | CF$_3$ | Cl | O | CH$_3$ | CH$_2$CH$_3$ |

EXAMPLE 7

Following the procedure of Example 1 or Example 4, oxalyl chloride and 2-[4-(2-quinolyloxy)phenoxy]propionic acid are reacted together to give the corresponding propionic acid chloride. The acid chloride is then added to the sodium salt of methylacetoacetate, giving methyl 2-acetyl-4-[4-(2-quinolyloxy)phenoxy]-3-oxopentanoate (XII; each of X' and X" is hydrogen).

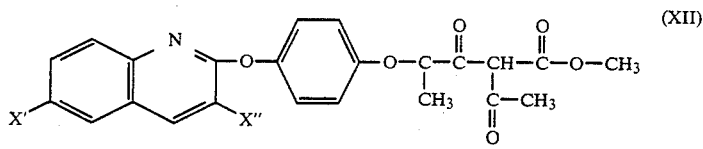
(XII)

The above pentanoate is heated with DMSO and sodium chloride, following Example 1 or Example 4 procedures, to yield the final product, 5-[4-(2-quinolyloxy)phenoxy]-2,4-hexanedione (XIII; each of X' and X" is hydrogen).

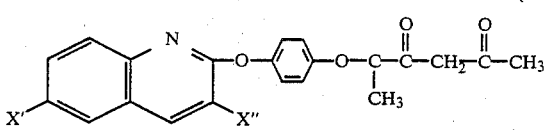
(XIII)

In the same manner, methyl 2-acetyl-4-[4-(6-fluoro-2-quinolyloxy)phenoxy]-3-oxopentanoate (XII; X' is fluoro and X" is hydrogen) is prepared from 2-[4-(6-fluoro-2-quinolyloxy)phenoxy]propionic acid chloride and the sodium salt of methylacetoacetate. This pentanoate is then heated with sodium chloride and DMSO to give 5-[4-(6-fluoro-2-quinolyloxy)phenoxy]2,4-hexanedione (XIII; X' is fluoro and X" is hydrogen).

EXAMPLE 8

Following the procedure of Example 1 or Example 4, oxalyl chloride and 2-[4-(2-quinoxalinyloxy)phenoxy]propionic acid are reacted together to give the corresponding propionic acid chloride. The acid chloride is then reacted with the sodium salt or methylacetoacetate to give methyl 2-acetyl-4-[4-(2-quinoxalinyloxy)phenoxy]-3-oxopentanoate (XIV; X' is hydrogen and X" is hydrogen).

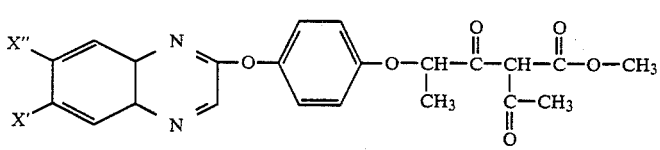
(XIV)

The above pentanoate is heated with sodium chloride and DMSO, following Example 1 or Example 4 procedures, to yield 5-[4-(2-quinoxalinyloxy)phenoxy]-2,4-hexanedione (XV; X' is hydrogen and X" is hydrogen).

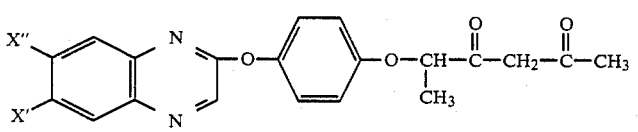
(XV)

In the same manner, methyl 2-acetyl-4-[4-(6-chloro-2-quinoxalinyloxy)phenoxy]-3-oxopentanoate (XIV; X' is chloro and X" is hydrogen) is prepared from 2-[4-(6-chloro-2-quinoxalinyloxy)phenoxy]propionic acid chloride and the sodium salt of methylacetoacetate. This pentanoate is then heated with sodium chloride and DMSO to yield 5-[4-(6-chloro-2-quinoxalinyloxy)-phenoxy]-2,4-hexanedione (XV; X' is chloro and X" is hydrogen).

Again, following the same procedures, methyl 2-acetyl-4-[4-(6,7-dichloro-2-quinoxalinyloxy)phenoxy]-3-oxopentanoate (XIV; X' is chloro and X" is chloro) is prepared from 2-[4-(6,7-dichloro-2-quinoxalinyloxy)-phenoxy]propionic acid chloride and the sodium salt of methylacetoacetate, and is then heated with sodium chloride and DMSO to yield 5-[4-(6,7-dichloro-2-quinoxalinyloxy)phenoxy]-2,4-hexanedione (XV; X' is chloro and X" is chloro).

EXAMPLE 9

Following the procedure of Example 1 or 4, 2-[4-(benzo-1,3-oxazolyl-2-oxy)phenoxy]propionic acid chloride is prepared from oxalyl chloride and the corresponding propionic acid. The acid chloride is then reacted with the sodium salt of methylacetoacetate to give methyl 2-acetyl-4-[4-(benzo-1,3-oxazolyl-2-oxy)-phenoxy]-3-oxopentanoate (XVI; Q is oxygen and X' is hydrogen).

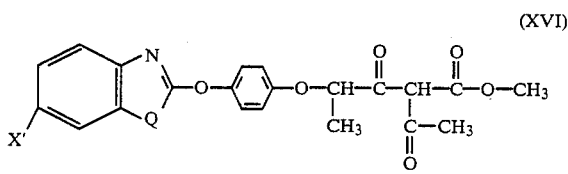
(XVI)

The above pentanoate is heated with sodium chloride and DMSO to give 5-[4-(benzo-1,3-oxazolyl-2-oxy)-phenoxy]-2,4-hexanedione (XVII; Q is oxygen and X' is hydrogen).

(XVII)

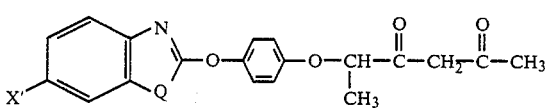

Following the same procedures, oxalyl chloride and 2-[4-(benzo-1,3-thiazolyl-2-oxy)phenoxy]propionic acid are reacted together to give the corresponding acid chloride, which is then reacted with the sodium salt of methylacetoacetate to give methyl 2-acetyl-4-[4-(benzo-1,3-thiazolyl-2-oxy)phenoxy]-3-oxopentanoate (XVI; Q is sulfur and X' is hydrogen). This oxopentanoate is heated with sodium chloride and DMSO to yield 5-[4-(benzo-1,3-thiazolyl-2-oxy)phenoxy]-2,4-hexanedione (XVII: Q is sulfur and X' is hydrogen).

EXAMPLE 10

Post-emergence herbicidal activity on the grasses green foxtail, watergrass, shattercane and wild oats was tested for the compound 5-[4-(4-trifluoromethylphenoxy)phenoxy]-2,4-hexanedione by spraying seedlings with a solution of water/acetone (1:1), surfactant (1%) and the test compound at a rate equivalent to 10 lb/acre. Scoring was made two weeks after spraying. The compound showed 100% herbicidal activity.

Pre-emergent herbicidal activity of the above compound was tested on the above-listed grasses at a rate equivalent to 10 lb/acre. Observation showed 100% herbicidal activity.

EXAMPLE 11

Following the procedure of Example 8, 2-[4-(6-fluoro-2-quinoxalinyloxy)phenoxy]propionic acid is reacted with oxalyl chloride to give the corresponding propionic acid chloride, which is then reacted with the sodium salt of methylacetoacetate to give methyl 2-acetyl-4-[4-(6-fluoro-2-quinoxalinyloxy)phenoxy]-3-oxopentanoate (XIV; X' is fluoro and X'' is hydrogen). This pentanoate is heated with sodium chloride and DMSO to give 5-[4-(6-fluoro-2-quinoxalinyloxy)phenoxy]-2,4-hexanedione (XV; X' is fluoro and X'' is hydrogen).

In the same manner, 2-[4-(6-trifluoromethyl-2-quinoxalinyloxy)phenoxy]propionic acid chloride is prepared from the corresponding propionic acid and oxalyl chloride, and is then reacted with the sodium salt of methylacetoacetate to give methyl 2-acetyl-4-[4-(6-trifluoromethyl-2-quinoxalinyloxy)phenoxy]-3-oxopentanoate (XIV; X' is CF$_3$ and X'' is hydrogen). The pentanoate is then heated with sodium chloride and DMSO to yield 5-[4-(6-trifluoromethyl-2-quinoxalinyloxy)phenoxy]-2,4-hexanedione (XV; X' is CF$_3$ and X'' is hydrogen).

EXAMPLE 12

To a solution of 1.06 g (2.94 mmol) of (R)-2-[4-(3-chloro-5-trifluoromethyl-2-pyridyloxy)phenoxy]propionic acid in 5 ml of dry ether under a nitrogen atmosphere and cooled to 0° is added 400 μl (5.50 mmol, 0.66 g) of thionyl chloride and 50 μl of DMF. After 5 hours at 0°, the reaction is stirred at RT overnight. The ether solution of acid chloride is then removed from the oily residue, and the ether and excess thionyl chloride are removed by rotoevaporation to give (R)-2-[4-(3-chloro-5-trifluoromethyl-2-pyridyloxy)phenoxy]propionic acid chloride.

A sodium salt solution of ethyl acetoacetate is prepared by adding 0.78 g (6.0 mmol) of ethyl acetoacetate to a suspension of 0.144 g (6.0 mmol) of sodium hydride in 15 ml of benzene. After hydrogen gas evolution has ceased, the suspension is cooled in an ice bath, and the above acid chloride in 5 ml of benzene is added dropwise. The reaction is heated to reflux for 3.5 hours. It is then cooled and poured into ether and dilute HCl solution. The organic phase is separated, and the aqueous fraction is re-extracted with ether. The organic fractions are combined, washed with brine and dried over sodium sulfate. The solvent is removed to give ethyl (R)-2-acetyl-4-[4-(3-chloro-5-trifluoromethyl-2-pyridyloxy)phenoxy]-3-oxopentanoate (XVIII; Q$^1$ is N, Y is chloro, Z is trifluoromethyl and R$^3$ is ethyl).

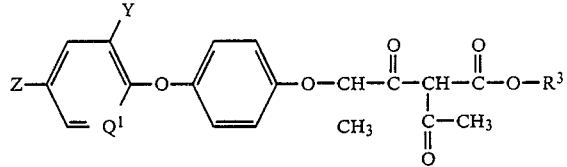

(XVIII)

To a solution of 1.4 g of the above pentanoate in 8 ml of DMSO and 0.2 ml of water is added 0.232 g (4.0 mmol) of sodium chloride. This mixture is heated at 165° for 1.5 hours and is then stirred at RT for 90 hours. The mixture is poured into dilute HCl and ether. The organic phase is separated, washed with water and with brine, and dried over sodium sulfate. The crude product is purified by prep. TLC to give (R)-5-[4-(3-chloro-5-trifluoromethyl-2-pyridyloxy)phenoxy]-2,4-hexanedione (XIX; Q$^1$ is N, Y is chloro and Z is trifluoromethyl). MS m/e 401 (M$^+$); specific rotation $[\alpha]_D^{20} = +2.9°$ (c=9.96 mg/ml CHCl$_3$).

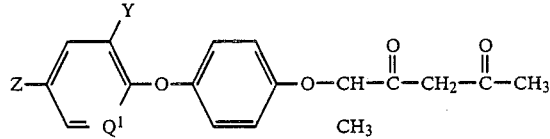

(XIX)

(R)-2-[4-(3-chloro-5-trifluoromethyl-2-pyridyloxy)phenoxy]propionic acid is prepared as follows: A suspension of ethyl (R)-2-mesyloxypropionate (0.392 g, 2.0 mmol), 4-(3-chloro-5-trifluoromethyl-2-pyridyloxy)phenol (0.578 g, 2.0 mmol) and potassium carbonate (0.276 g, 2.0 mmo.) in 8 ml of DMSO is heated at 80° for 24 hours. The reaction mixture is cooled and worked up to give ethyl (R)-2-[4-(3-chloro-5-trifluoromethyl-2-pyridyloxy)phenoxy]propionate. The propionate is hydrolyzed by stirring it (0.80 g, 2.22 mmol) in 10 ml of ethanol with sodium hydroxide (0.10 g, 2.50 mmol) in 1 ml of water overnight. The ethanol is then removed in vacuo from the reaction mixture. The residue is acidified with HCl and extracted with ether. The organic fraction is washed with brine until neutral and dried over sodium sulfate. Solvent is removed to give (R)-2-[4-(3-chloro-5-trifluoromethyl-2-pyridyloxy)phenoxy]propionic acid.

EXAMPLE 13

Following the procedure of Example 12, (R)-2-[4-(3,5-dichloro-2-pyridyloxy)phenoxy]propionic acid chloride is prepared from (R)-2-[4-(3,5-dichloro-2-pyridyloxy)phenoxy]propionic acid (1.15 g, 3.50 mmol) and oxalyl chloride (0.6 ml) in ether (10 ml) and DMF (2 drops).

The above acid chloride, in benzene (10 ml), is added dropwise to the chilled sodium salt of ethyl acetoacetate, prepared from sodium (0.096 g) and ethyl acetoacetate (0.546 g, 4.20 mmol), again following Example 12 procedures, to give ethyl (R)-2-acetyl-4-[4-(3,5-dichloro-2-pyridyloxy)phenoxy]-3-oxopentanoate (XVIII; $Q^1$ is N, each of Y and Z is chloro and $R^3$ is ethyl).

The above pentanoate, in DMSO (6 ml) and water (0.2 ml), is heated with sodium chloride (0.175 g) at 165° for 0.5 hour. The reaction is diluted with ether and washed, dried and evaporated to dryness. The crude product is purified by prep. TLC to give (R)-5-[4-(3,5-dichloro-2-pyridyloxy)phenoxy]-2,4-hexanedione (XIX; $Q^1$ is N, and each of Y and Z is chloro). MS m/e 368 (M+); specific rotation $[\alpha]_D^{25} = +0.96°$ (c=10 mg/ml in CHCl₃).

Following the above procedures, (R)-2-[4-(5-trifluoromethyl-2-pyridyloxy)phenoxy]propionic acid chloride, prepared from (R)-2-[4-(5-trifluoromethyl-2-pyridyloxy)phenoxy]propionic acid and thionyl chloride, is reacted with the sodium salt of ethyl acetoacetate to give ethyl (R)-2-acetyl-4-[4-(5-trifluoromethyl-2-pyridyloxy)phenoxy]-3-oxopentanoate (XVIII: $Q^1$ is N, Y is hydrogen, Z is trifluoromethyl and $R^3$ is ethyl). This pentanoate is then heated with sodium chloride to give (R)-5-[4-(5-trifluoromethyl-2-pyridyloxy)phenoxy]2,4-hexanedione (XIX; $Q^1$ is N, Y is hydrogen and Z is trifluoromethyl).

EXAMPLE 14

Following the procedure of Example 12, (R)-2-[4-(4-trifluoromethylphenoxy)phenoxy]propionic acid chloride is prepared from (R)-2-[4-(4-trifluoromethylphenoxy)phenoxy]propionic acid (1.0 g, 3.06 mmol) and oxalyl chloride (0.6 ml) in ether (10 ml) and DMF (2 drops). The acid chloride is then reacted with the sodium salt of ethyl acetoacetate (0.084 g of sodium and 0.480 g of ethyl acetoacetate) to give ethyl (R)-2-acetyl-4-[4-(4-trifluoromethylphenoxy)phenoxy]-3-oxopentanoate (XVIII; $Q^1$ is CH, Y is hydrogen, Z is trifluoromethyl and $R^3$ is ethyl).

The above pentanoate is heated to 165° for 0.5 hour, in the presence of sodium chloride (0.175 g), DMSO (6 ml) and water (0.2 ml) to give (R)-5-[4-(4-trifluoromethylphenoxy)phenoxy]-2,4-hexanedione (XIX; $Q^1$ is CH, Y is hydrogen and Z is trifluoromethyl). MS m/e 366 (M+); specific rotation $[\alpha]_D^{20} = +0.84°$ (c=10 mg/ml in CHCl₃).

EXAMPLE 15

Following the procedure of Example 10, each of the compounds (R)-5-[4-(4-trifluoromethylphenoxy)phenoxy]-2,4-hexanedione (cpd. A), (R)-5-[4-(3,5-dichloro-2-pyridyloxy)phenoxy]-2,4-hexanedione (cpd. B) and (R)-5-[4-(3-chloro-5-trifluoromethyl-2-pyridyloxy)phenoxy]-2,4-hexanedione (cpd. C) was tested for pre- and post-emergence herbicidal activity on grasses. The results are given in Table E below.

TABLE E

| | Herbicidal Activity Against Grasses at 10 lb/Acre | |
|---|---|---|
| | % Activity | |
| Cpd. | Pre | Post |
| A | 99 | 100 |
| B | 100 | 100 |
| C | 100 | 100 |

EXAMPLE 16

A. To a solution of acetone N,N-dimethylhydrazone (0.32 g, 3.23 mmol) in tetrahydrofuran (THF; 5 ml) is added N-butyllithium (0.21 g, 3.23 mmol) at −65°, and the mixture is stirred for 30 minutes. To this is added dropwise 2-[4-(4-trifluoromethylphenoxy)phenoxy]propanal (1.0 g, 3.23 mmol) in 5 ml of THF, keeping the temperature at or below −60°. After 3 hours at −65°, the reaction mixture is allowed to warm to 0°, and is poured onto 20 g ice made slightly acidic with 10% acetic acid. It is extracted into ether, and the organic extract is washed with water and with NaCl and is dried over sodium sulfate. Solvent is removed, and the residue is purified by prep. TLC (silica gel, 20% ethyl acetate/hexane) to give 4-hydroxy-5-[4-(4-trifluoromethylphenoxy)phenoxy]-2-hexanone (C'; $Q^1$ is CH, Y is hydrogen, Z is trifluoromethyl, $R^1$ is methyl and $R^2$ is methyl).

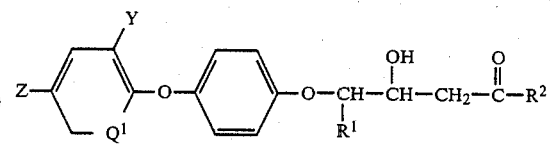

(C')

B. To a stirred solution of N-chlorosuccinimide (0.40 g, 3 mmol) in toluene (10 ml) at −10° under argon is added dimethylsulfide (0.3 ml, 4 mmol). The mixture is cooled to −25°, and 4-hydroxy-5-[4-(4-trifluoromethylphenoxy)phenoxy]-2-hexanone (2 mmol) in several ml of toluene is added dropwise. After 2 hours at −25°, the mixture is cooled to −60°, and a solution of 0.31 g (3 mmol) of triethylamine in several ml of toluene is added dropwise. The reaction mixture is allowed to slowly warm to RT and is quenched by the addition of 5 ml of water. The mixture is poured into ether, and the organic fraction is then separated, washed with 5% HCl, water and brine, and dried over sodium sulfate. Solvent is removed and the residue is purified by prep. TLC to give 5-[4-(4-trifluoromethylphenoxy)phenoxy]-2,4-hexanedione (IX; Z is trifluoromethyl, Y is hydrogen, W is oxygen, $R^1$ is methyl and $R^2$ is methyl).

EXAMPLE 17

To a solution of acetone N,N-dimethylhydrazone (0.48 g, 4.8 mmol) in 5 ml of THF is added N-butyllithium (4.8 mmol) at −65°, and the mixture is stirred for about 30 minutes. 2-[4-(3-chloro-5-trifluoromethyl-2-pyridyloxy)phenoxy]propanal (1.50 g, 4.8 mmol) in 5 ml of THF is added dropwise. After several hours at −65°, the reaction mixture is allowed to warm to 0° and is poured onto ice made slightly acidic with 10% acetic acid. The organic phase is separated, washed with water and with NaCl and dried. Solvent is removed to give 4-hydroxy-5-[4-(3-chloro-5-trifluoromethyl-2-pyridyloxy)phenoxy]-2-hexanone N,N-dimethylhydrazone.

The above hexanone hydrazone (1 mmol) is dissolved in 10 ml of methanol with 2 ml of 2M pH 7 phosphate buffer, and a solution of sodium periodate (2.2 mmol) in 2 ml of water is added, with stirring. The mixture is stirred for 3 hours, after which the solvent is removed and the residue is extracted with chloroform. The extract is washed with water and dried and the solvent is removed to give 4-hydroxy-5-[4-(3-chloro-5-trifluoromethyl-2-pyridyloxy)phenoxy]-2-hexanone (C'; $Q^1$ is N, Y is chloro, Z is trifluoromethyl, $R^1$ is methyl and $R^2$ is methyl).

Following the procedure of Example 16B, the above hydroxy hexanone is oxidized to give 5-[4-(3-chloro-5- trifluoromethyl-2-pyridyloxy)phenoxy]-2,4-hexanedione (XI; Z is trifluoromethyl, Y is chloro, W is oxygen, R¹ is methyl and R² is methyl).

EXAMPLE 18

Following the procedure of Example 17, the lithium salt of acetone N,N-dimethylhydrazone is reacted with each of the propanals under column III to give the N,N-dimethylhydrazone of the β-hydroxy ketone, which is then hydrolyzed to the corresponding ketone under column IV, which is then oxidized to the corresponding alkanedione under column V.

III 28. 2-[4-(6-fluoro-2-quinolyloxy)phenoxy]propanal.
29. 2-[4-(6-chloro-2-quinolyloxy)phenoxy]propanal.
30. 2-[4-(6-fluoro-2-quinoxalinyloxy)phenoxy]propanal.
31. 2-[4-(6-chloro-2-quinoxalinyloxy)phenoxy]propanal.
32. 2-[4-(6,7-dichloro-2-quinoxalinyloxy)phenoxy]propanal.
33. 2-[4-(6-chloro benzo-1,3-oxazolyl-2-oxy)phenoxy]propanal.
34. 2-[4-(6-chloro benzo-1,3-thiazolyl-2-oxy)phenoxy]propanal.

IV 28. 4-hydroxy-5-[4-(6-fluoro-2-quinolyloxy)phenoxy]-2-hexanone.
29. 4-hydroxy-5-[4-(6-chloro-2-quinolyloxy)phenoxy]-2-hexanone.
30. 4-hydroxy-5-[4-(6-fluoro-2-quinoxalinyloxy)phenoxy]-2-hexanone.
31. 4-hydroxy-5-[4-(6-chloro-2-quinoxalinyloxy)phenoxy]-2-hexanone.
32. 4-hydroxy-5-[4-(6,7-dichloro-2-quinoxalinyloxy)phenoxy]-2-hexanone.
33. 4-hydroxy-5-[4-(6-chloro benzo-1,3-oxazolyl-2-oxy)phenoxy]-2-hexanone.
34. 4-hydroxy-5-[4-(6-chloro benzo-1,3-thiazolyl-2-oxy)phenoxy]-2-hexanone.

V 28. 5-[4-(6-fluoro-2-quinolyloxyphenoxy)]-2,4-hexanedione (XIII; X' is fluoro and X" is hydrogen).
29. 5-[4-(6-chloro-2-quinolyloxyphenoxy)]-2,4-hexanedione (XIII; X' is chloro and X" is hydrogen).
30. 5-[4-(6-fluoro-2-quinoxalinyloxy)phenoxy]-2,4-hexanedione (XV; X' is fluoro and X" is hydrogen).
31. 5-[4-(6-chloro-2-quinoxalinyloxy)phenoxy]-2,4-hexanedione (XV; X' is chloro and X" is hydrogen).
32. 5-[4-(6,7-dichloro-2-quinoxalinyloxy)phenoxy]-2,4-hexanedione (XV; each of X' and X" is chloro).
33. 5-[4-(6-chlorobenzo-1,3-oxazolyl-2-oxy)phenoxy]-2,4-hexanedione (XVII; Q is oxygen and X' is chloro).
34. 5-[4-(6-chlorobenzo-1,3-thiazolyl-2-oxy)phenoxy]-2,4-hexanedione (XVII; Q is sulfur and X' is chloro).

What is claimed is:

1. A compound of the following formula (A):

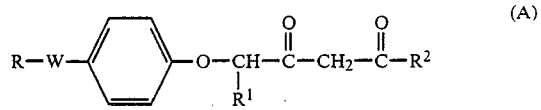

wherein,
R is

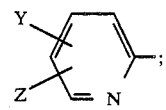

$R^1$ is hydrogen or lower alkyl;
$R^2$ is lower alkyl;
W is oxygen, sulfur or amino; and
each of Y and Z is independently hydrogen, lower alkyl, lower haloalkyl, lower alkoxy, halogen or nitro.

2. A compound of the following formula, according to claim 1:

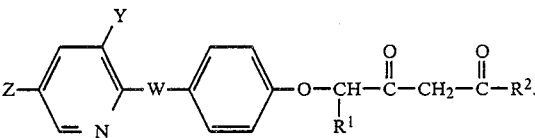

3. A compound according to claim 2 wherein W is oxygen, $R^1$ is methyl and $R^2$ is methyl or ethyl.
4. A compound according to claim 3 wherein Y is hydrogen or chloro and Z is chloro or trifluoromethyl.
5. The compound 5-[4-(5-trifluoromethyl-2-pyridyloxy)phenoxy]-2,4-hexanedione, according to claim 4.
6. The compound 5-[4-(3-chloro-5-trifluoromethyl-2-pyridyloxy)phenoxy]-2,4-hexanedione, according to claim 4.
7. The compound (R)-5-[4-(5-trifluoromethyl-2-pyridyloxy)phenoxy]-2,4-hexanedione, according to claim 4.
8. The compound (R)-5-[4-(3-chloro-5 trifluoromethyl-2-pyridyloxy)phenoxy]-2,4-hexanedione, according to claim 4.
9. A method for the control of weeds which comprises treating the weed or its locus with a herbicidally effective amount of a compound of formula (A) as disclosed in claim 1.

* * * * *